United States Patent
Liu

(10) Patent No.: US 9,035,089 B2
(45) Date of Patent: May 19, 2015

(54) MODIFIED CARBON MATERIAL AND PROCESS OF MAKING AND USING THE SAME

(75) Inventor: Ping Liu, Irvine, CA (US)

(73) Assignee: GM Global Technology Operations LLC, Detroit, MI (US)

(*) Notice: Subject to any disclaimer, the term of this patent is extended or adjusted under 35 U.S.C. 154(b) by 839 days.

(21) Appl. No.: 13/230,054

(22) Filed: Sep. 12, 2011

(65) Prior Publication Data

US 2013/0066105 A1    Mar. 14, 2013

(51) Int. Cl.
*C07C 309/00* (2006.01)
*C07C 309/10* (2006.01)

(52) U.S. Cl.
CPC ........... *C07C 309/10* (2013.01); *C07B 2200/11* (2013.01)

(58) Field of Classification Search
CPC .................................................... C07C 309/03
USPC ........................................................ 562/111
See application file for complete search history.

(56) References Cited

U.S. PATENT DOCUMENTS 5,554,739 A    9/1996   Belmont
6,042,643 A    3/2000   Belmont et al.
6,630,268 B2   10/2003  Tosco et al.

OTHER PUBLICATIONS

Xu et al., Electrochem Solid-State Letts, 8, A492-A494 (2005).*
Chen et al., J. Mater. Res., 13, 2423-2431 (1998).*
Hart, Science. 223(4639):883-7 (1984).*
Xu et al, Electrochem Solid-State Letts, 8, A492-A494 (2005)).*
Xu et al., Electrochemical and Solid State Letters, 6 (9) A 171-A173 (2003).
Pandurangappa et al. Analyst. 127, 1568-1571 (2002).
Barbier et al., J. Electrochem. Soc., 1990, 137, 1757.
A.J. Downard, Electroanalysis, 2000,12, 1085.
Saab et al. (J. Electrochem. Soc., 150, 2003, A214-A218).
Qi et al. (Electrochem. Solid State Lett., 6. A492-A494:8. A313-A315:6 A171-A173), (2005).

* cited by examiner

*Primary Examiner* — Sudhakar Katakam
*Assistant Examiner* — Kofi Adzamli
(74) *Attorney, Agent, or Firm* — BrooksGroup

(57) ABSTRACT

A method of making modified carbon materials for use in fabricating fuel cell components. The modified carbon may comprise pendant fluorocarbon groups bonded covalently bonded thereto. In one embodiment, a mixture is formed and comprises carbon material suitable for use in a fuel cell component, an organic solvent, a compound having the general formula I—R wherein R is a fluorocarbon, and a reductant.

20 Claims, 2 Drawing Sheets

MODIFIED CARBON MATERIAL AND PROCESS OF MAKING AND USING THE SAME

TECHNICAL FIELD

The field of the invention generally relates to includes modified carbon materials and methods of making and using the same.

BACKGROUND OF THE INVENTION

Carbon may be utilized in numerous fashions within the fuel cell industry. For example, carbon materials are commonly used to fabricate a variety of fuel cell components. It is oftentimes desirable to modify these carbon materials in an attempt to improve their performance as part of a fuel cell component in a fuel cell environment. For example, it may be beneficial to alter, among other properties, a particular fuel cell component's affinity towards water by rendering it more hydrophobic or more hydrophilic.

SUMMARY OF THE INVENTION

In one embodiment of the invention, a carbon material suitable for use in a fuel cell component is provided. The carbon material, an organic solvent, a compound having the formula I—R, and a reductant are formed into a mixture and agitated.

In another embodiment of the invention, R comprises a perfluorocarbon group in the compound having the general formula I—R.

In yet another embodiment of the invention, R comprises a perfluorosulfonic acid precursor group in the compound having the general formula I—R.

In still yet another embodiment of the invention, a fuel cell component comprises pendant fluorocarbon groups covalently bonded thereto.

Other exemplary embodiments of the disclosure will become apparent from the detailed description. It should be understood that the detailed description and specific examples, while indicating the exemplary embodiments of the disclosure, are intended for illustration purposes only and not intended to limit the scope of the invention.

BRIEF DESCRIPTION OF THE DRAWINGS

The disclosure will now be described, by way of example, and not limitation, with reference to the accompanying drawings. The following is a brief description of the drawings.

DETAILED DESCRIPTION OF EXEMPLARY EMBODIMENTS

The description of the following embodiment(s) is merely exemplary in nature and is in no way intended to limit the claimed invention, its application, or its uses.

In general, a carbon material may be chemically altered to form a modified carbon material having a pendant fluorocarbon group. The modified carbon material may be used for fabricating a fuel cell component. To make the modified carbon material, a covalent carbon-carbon bond may be formed between a fluorocarbon and the carbon material in the presence of a reductant. The fluorocarbon group may comprise, for example, a perfluorocarbon group or a perfluorosulfonic acid group because of their demonstrated thermal, chemical, and electrochemical stability in various fuel cell environments. Likewise, these fluorocarbons may improve water management and performance of the fuel cell component, reduce the corrosion rate of the fuel cell component, improve stability and uniformity of the fuel cell component, and reduce the reliance on materials such as polytetrafluoroethylene (PTFE) or Nafion to alter the fuel cell components affinity towards water.

Figure 1:
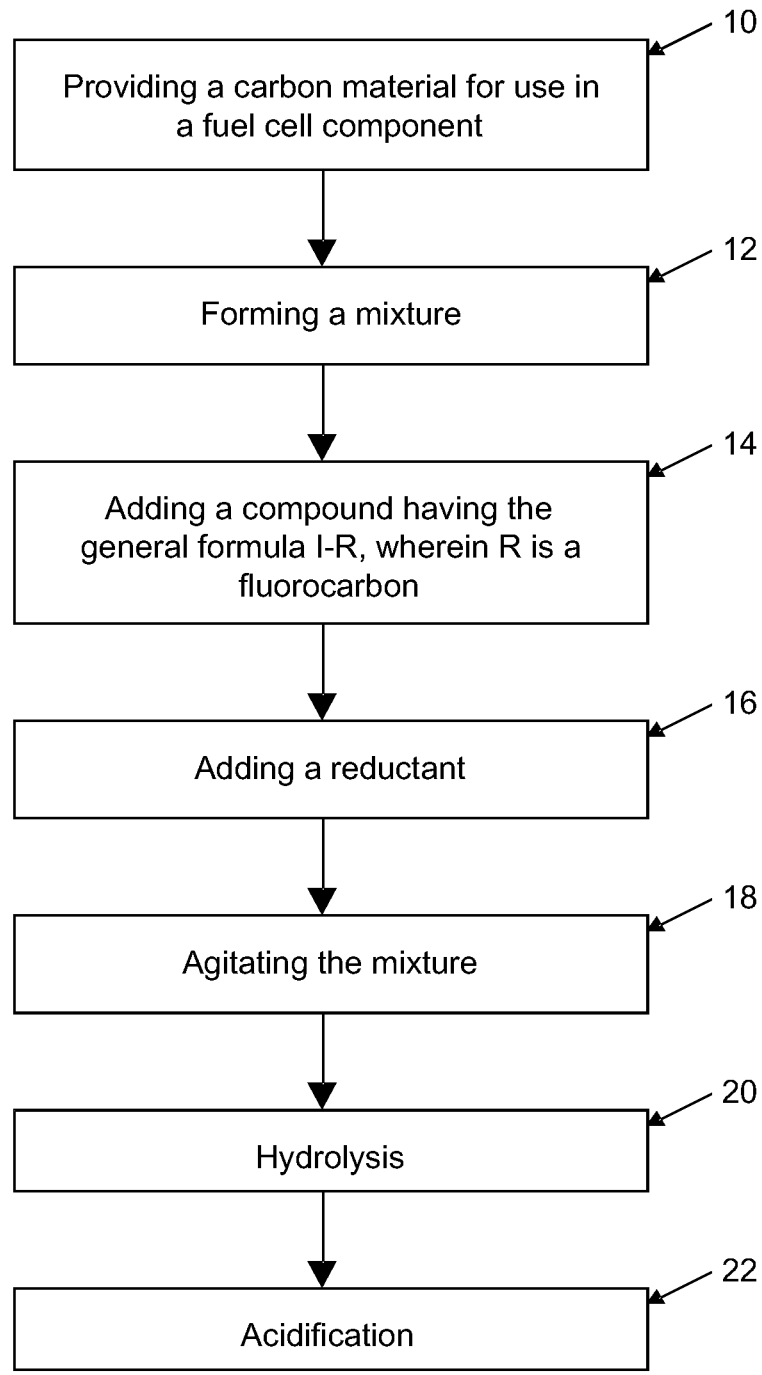
FIG. 1 is a flowchart illustrating a method of forming a modified carbon material according to various embodiments of the invention.

Referring now to the drawings, FIG. 1 shows one embodiment of a method for forming a modified carbon material for use in fabricating a fuel cell component, and generally includes i.) forming a mixture that comprises a carbon material, an organic solvent, a compound having the formula I—R wherein R is a fluorocarbon, and a reductant, and ii.) agitating the mixture. Additional steps may be required depending on whether R comprises a perfluorocarbon group for ultimately rendering the fuel cell component more hydrophobic, or a perfluorosulfonic acid precursor group capable of conversion into a perfluorosulfonic acid group for ultimately rendering the fuel cell component more hydrophilic.

Figure 2:
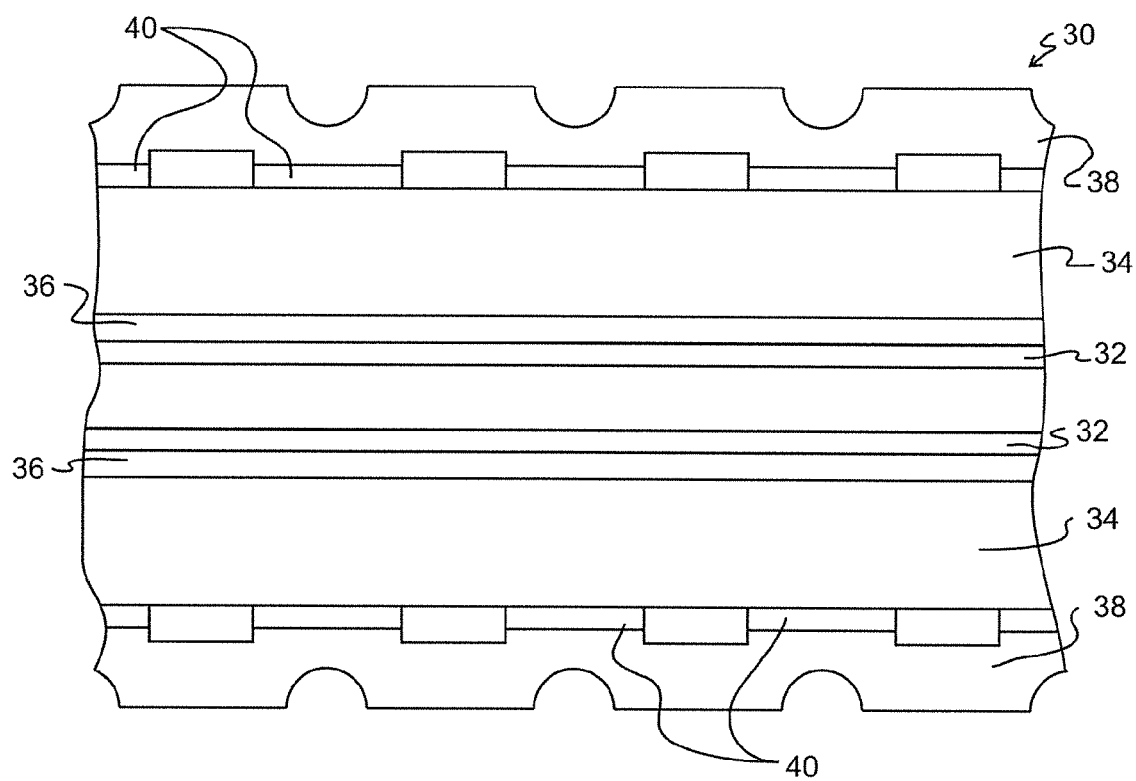
FIG. 2 illustrates a fuel cell including various fuel cell components that may comprise a modified carbon material according to various embodiments of the invention.

In a first example embodiment, a carbon material suitable for use in a proton exchange membrane (PEM) fuel cell component is provided, as depicted in step 10. Such carbon materials are generally known in the art and are normally used in the manufacture of various components of a PEM fuel cell 30 including, for example, an electrode layer 32, a gas diffusion media layer (GDML) 34, a microporous layer 36, and a bipolar plate 38, as best shown in FIG. 2. Although a PEM fuel cell 30 and some of its components are described in this embodiment, those skilled in the art will appreciate that similar carbon materials are used to fabricate components in other types of fuel cells such as direct methanol fuel cells and alkaline electrolyte fuel cells.

The electrode layer 32 generally comprises small catalyst particles mixed with a binder such as an ionomer. The ionomer may be an ionic conduction polymer such as Nafion from DuPont™ (www.dupont.com) or any other suitable ionomer as appreciated by one skilled in the art. Platinum metals and platinum alloys are popular examples of catalyst particles and may be utilized as either a pure catalyst or a supported catalyst. In the case of a supported catalyst, the small catalyst particles may be finely divided over larger carbon or graphite support particles. Vulcan XC72 carbon powder is widely used to support catalyst particles and is available from Cabot Corporation (www.cabot-corp.com) under the trade designation CABOT®.

Typically, the carbon materials that make up the GDML 34 include, but are not limited to, carbon cloth, non-woven pressed carbon fibers, carbon paper, or a felt-like carbon material. Examples of carbon-based materials that may be useful in constructing the GDML 34 include, among others, ELAT carbon paper, TORAY carbon paper, SGL SIGRACET®, Mitsubishi Rayon (Mitsubishi Rayon Co., Ltd.,) AFN non-woven carbon cloth, ZOLTEK carbon cloth, high surface area carbon such as Ketjen Black or Graphitized Vulcan, or carbon nanotubes or carbon nanofibers.

The microporous layer 36 may comprise a carbon-based binder and some components which may influence the binder's affinity towards water. The carbon-based binder may be Vulcan XC72 or other carbon materials known in the art, including, among others, ELAT carbon paper, TORAY carbon paper, SGL SIGRACET®, Mitsubishi Rayon (Mitsubishi Rayon Co., Ltd.,) AFN non-woven carbon cloth, ZOLTEK carbon cloth, high surface area carbon such as Ketjen Black or Graphitized Vulcan, or carbon nanotubes or carbon nanofibers. The microporous layer 36 may comprise a carbon black/fluorinated polymer matrix which may be coated onto the gas diffusion media substrate. The microporous layer 36 may also comprise a hydrophobic agent such as, but not limited to, a fluorinated polymer such as PTFE or FEP. The fluorinated polymer may comprise dispersions such as DuPont™ Teflon® PTFE Grade 30 Aqueous Dispersion comprising approximately 60% (by total weight) of 0.05 to 0.5 mm polytetrafluoroethylene (PTFE) resin particles suspended in water. Additional fluorinated polymers are available through chemical companies such as 3M™ and the like. CARBEL®, a gas diffusion media product, readily commercially available from W. L. Gore & Associates, Inc. (Newark, Del.), may be considered as a stand-alone MPL-like material.

Bipolar plates 38 are usually made of a conductive material such as, but not limited to, graphite, a polymeric carbon composite, or metals such as stainless steel, aluminum, titanium, or combinations thereof. An additional conductive layer 40 is oftentimes applied to the surface of metal bipolar plates to protect against corrosion while still maintaining electrical and thermal conductivity. The conductive layer 40 may be formed from carbon materials such as carbon black or graphite, or other similar materials known in the art.

Referring back to FIG. 1 and as shown in step 12, a mixture is formed by mixing the carbon material suitable for use in a fuel cell component with an organic solvent. The organic solvent may be any known and/or commercially available organic solvent capable of dissolving the particular carbon material being modified, and will be apparent to those skilled in the art. Examples of such solvents include, but are not limited to, dimethylsulfur oxide, dichloromethane, dimethylformide, and combinations thereof.

As shown in step 14, a compound having the formula I—R may be added to the mixture. The compound may be added to the mixture in a predetermined amount that produces a ratio of R to carbon material between about 0.25 mmol/g and about 5.0 mmol/g. In this particular embodiment, I is iodine and R is a fluorocarbon comprising a perfluorocarbon molecule having the general formula $C_nF_{2n}$, wherein $n \geq 1$.

As shown in step 16, a reductant may be added to the mixture. The reductant may be any substance that increases the mixture's concentration of free radical R groups. For example, when dissolved in the mixture, sodium hydrosulfite ($Na_2S_2O_4$) generates free radical initiators upon thermal decomposition. The free radical initiators then attack the I—R compounds to form free radical R groups which, in turn, react with the carbon material. This results in the carbon material having pendant R groups bonded thereto through a covalent carbon-carbon bond. Thus, in this embodiment, the modified carbon material comprises pendant fluorocarbon groups each of which comprises a perfluorocarbon group ($C_nF_{2n}$). Other suitable reductants that can be used include, but are not limited to, copper.

As shown in step 18, the mixture may be agitated to facilitate the formation of the modified carbon material. In this embodiment, the mixture may be stirred for a period of one to ten days while maintaining the mixture at a temperature between about 0° C. and 100° C. In general, the stirring period and the mixture temperature can vary within these ranges as a result of known process parameters. In any event, approximately two to six days of stirring is advisable when the mixture temperature is maintained between about 20° C. and about 60° C.

Next, the modified carbon material may be separated from the mixture. For instance, the mixture may be separated by any technique known to those skilled in the art, such as filtration or centrifugation. Once separated, the modified carbon material may be washed with dichloromethane and/or acetone to remove any unwanted impurities.

As mentioned before, the modified carbon material of this embodiment comprises pendant fluorocarbon groups each comprising a perfluorocarbon group. This modified carbon material may now be fabricated into a particular fuel cell component by any one of a variety of known methods and subsequently used in a PEM fuel cell. The presence of the perfluorocarbon groups will render the fuel cell component more hydrophobic than an equivalent component fabricated from the original non-modified carbon material.

In a second example embodiment is similar to the first example embodiment in many respects, and the similarities will not be repeated in detail here. A difference here is that, in the compound I—R, R is a fluorocarbon comprising a perfluorosulfonic acid precursor group having a sulfonyl fluoride end group ($SO_2F$). For example, the perfluorosulfonic acid precursor group may have the general formula $C_nCF_{2n}OC_nF_{2n}SO_2F$, wherein $1 \leq n \leq 10$. In another example the perfluorosulfonic acid group may have the general formula $C_nF_{2n}SO_2F$, wherein $1 \leq n \leq 10$. The perfluorosulfonic acid precursor group may be added to the mixture in the same ratio as set forth in the first embodiment.

Furthermore, in this embodiment, additional steps are utilized to convert the perfluorosulfonic acid precursor group into a perfluorosulfonic acid group following the agitation step, and generally include a hydrolysis step and an acidification step, as shown in FIG. 1. Although these steps are demonstrated below using specific materials, those skilled in the art understand that other materials can achieve similar results in a similar fashion.

The hydrolysis reaction, as shown in step 20, converts the sulfonyl fluoride end group into an end group comprising a sulfonate functional group ($SO_2O^-$). For example, in this embodiment, the hydrolysis reaction may convert the sulfonyl fluoride end group into a metal sulfonate end group having the general formula $SO_3M$, wherein M is Li, Na, or K. Of course, M may be a variety of other atoms or groups such as, for example, tetraalkylammonium. One particular way to convert the sulfonyl fluoride end group of the perfluorosulfonic precursor molecule into a metal sulfonate end group includes adding the modified carbon material to a mixture comprising sodium hydroxide, an organic solvent such as dimethylsulfur oxide, and water. Sodium hydroxide should be added to the mixture in a sufficient stoichiometric amount to ensure that enough Na is present to react with the sulfonyl fluoride end groups of the modified carbon material to form $NaSO_3$ end groups. The mixture may be maintained at a temperature between about 60° C. and 80° C. and stirred for about three to about seven hours to allow the reaction to proceed. Afterwards the mixture may be separated by any known and appropriate technique such as filtration or centrifugation. Once separated, the modified carbon material may be washed with water to remove any impurities, The acidification reaction, as shown in step 22, converts the end group comprising the sulfonate functional group into a sulfonic acid group ($SO_3H$). One particular way to convert the $NaSO_3$ end group of the above example into sulfonic acid end group includes adding the modified carbon material to acidic solution capable of replacing the sodium atom with a hydrogen atom. For example, the modified carbon material may be added to 15% nitric acid ($HNO_3$) and the mixture stirred for about 14 hours to about 18 hours at room temperature. Those skilled in the art will appreciate that other acidic solutions may be used and, accordingly, stirring times and mixture temperatures may vary. Afterwards the mixture may be separated by any known and appropriate technique such as filtration or centrifugation. Once separated, the modified carbon material may be washed with water to remove any impurities and then dried. The modified carbon material now comprises pendant perfluorosulfonic acid groups.

This modified carbon material may now be fabricated into a particular fuel cell component by any one of a variety of known methods and subsequently used in a PEM fuel cell. The presence of the perfluorosulfonic acid groups will render the fuel cell component more hydrophilic and thus more ionically conductive than an equivalent component fabricated from the original non-modified carbon material.

Example 1 demonstrates a method for forming a modified carbon material having pendant perfluorosulfonic acid groups attached thereto through carbon-carbon covalent bonds.

Example 1

1.5 grams of Vulcan XC-72 carbon was dried over night at 100° C. The dried carbon was added to a nitrogen glovebox along with a 100 mL of solvent that comprised dimethylsulfur oxide and dichloromethane. The dimethylsulfur oxide and dichloromethane were present in a 1:1 ratio by volume, which in this case is 50 mL each. To this solution, 3 mmol of $ICF_2CF_2OCF_2CF_2SO_2F$ was added. Next, 3 mmol of $NaHCO_3$ was added to the solution. After that, 3 mmol of $Na_2S_2O_4$ was added to the solution to serve as the reductant. The solution comprising the carbon, solvent, compound of the fluorinated functional group, and reductant was maintained at 20° C. and stirred for 2.5 days. After stirring, the carbon was filtered and washed with the cleansing solvents dichloromethane and acetone. A fluorine analysis of the carbon revealed a fluorine content of 1.7 weight percent.

The carbon was then added to a solution comprising 15 grams of NaOH, 35 grams of dimethylsulfur oxide, and 50 grams of water. The solution was heated to and maintained at 70° C. for about five hours while the hydrolysis reaction occurred. After the hydrolysis reaction the solution was centrifuged and washed with water.

The product from the hydrolysis reaction was added to a 100 mL solution comprising 15% $HNO_3$. The solution was stirred for sixteen hours after which it was centrifuged, washed with water, and dried. A fluorine analysis of this material revealed a fluorine content of 0.93 weight percent.

While exemplary embodiments of the disclosure have been described above, it will be recognized and understood that various modifications can be made by those of ordinary skill in the art. The appended claims are intended to cover all such modifications which may fall within the spirit and scope of the invention.

What is claimed is:
1. A method comprising:
providing a carbon material suitable for use in a fuel cell component;
forming a mixture by mixing the carbon material with an organic solvent;
adding a compound with the formula I—R, wherein R comprises a fluorocarbon;
adding a reductant to the mixture; and
agitating the mixture for a time period sufficient to generate radicals of .R which form carbon-carbon covalent bonds with the carbon material to form a modified carbon material.
2. A method as set forth in claim 1 wherein the fluorocarbon renders the modified carbon material more hydrophobic.

3. A method as set forth in claim 1 wherein the fluorocarbon renders the modified carbon material more hydrophilic.
4. A method as set forth in claim 1 wherein adding a compound with the formula I—R comprises adding an amount of the compound I—R such that the ratio of R to carbon material is about 0.25 mmol/g to about 5 mmol/g.
5. A method as set forth in claim 1 wherein agitating the mixture comprises agitating the mixture at a temperature between about 0° C. and about 100° C. for a time period between about 1 day and about 10 days.
6. A method as set forth in claim 1 wherein adding a compound with the formula I—R comprises adding a compound wherein R comprises a perfluorocarbon having the general formula $C_nF_{2n}$, where $n \geq 1$.
7. A method as set forth in claim 1 wherein adding a compound with the formula I—R comprises adding a compound wherein R comprises a perfluorosulfonic acid precursor group comprising a sulfonyl fluoride end group.
8. A method as set forth in claim 7 wherein adding a compound with the formula I—R comprises adding a compound wherein R comprises a perfluorosulfonic acid precursor group having the general formula $C_nF_{2n}SO_2F$, wherein $1 \leq n \leq 10$.
9. A method as set forth in claim 7 wherein adding a compound with the formula I—R comprises adding a compound wherein R comprises a perfluorosulfonic acid precursor molecule having the general formula $C_nF_{2n}OC_nF_{2n}SO_2F$, wherein $1 \leq n \leq 10$.
10. A method as set forth in claim 7 further comprising:
subjecting the modified carbon material to a hydrolysis reaction to convert the sulfonyl fluoride end group to an end group comprising a sulfonate functional group having the general formula $SO_3M$, wherein M comprises Li, Na, K, or tetraalkylammonium; and
subjecting the modified carbon material to an acidification reaction to convert the end group comprising a sulfonate functional group to a sulfonic acid end group.
11. A method as set forth in claim 10 wherein subjecting the perfluorosulfonic acid precursor group to a hydrolysis reaction comprises mixing the modified carbon material with water, an organic solvent, and a metal hydroxide.
12. A method as set forth in claim 10 wherein the subjecting the perfluorosulfonic acid precursor group to an acidification reaction comprises mixing the carbon material with an acid.
13. A method as set forth in claim 1 wherein providing the carbon material suitable for use in a fuel cell component comprises providing at least one of graphite, carbon black, vitreous carbon, activated charcoal, carbon aerogel, carbon fiber, or activated carbon.
14. A method as set forth in claim 1 wherein forming a mixture by mixing the carbon material with an organic solvent comprises mixing the carbon material with at least one of dimethylsulfur oxide, dichloromethane, dimethylformide, acetonitrile, propylene carbonate, ethylene carbonate, or diethyl carbonate.
15. A method as set forth in claim 1 wherein adding a reductant to the mixture comprises adding at least one of sodium hydrosulfite ($Na_2S_2O_4$) or copper.
16. A method comprising:
forming a mixture by mixing a carbon material suitable for use in a fuel cell component, an organic solvent, a reductant, and a compound having the general formula $IC_nF_{2n}$ in an amount such that the ratio of $C_nF_{2n}$ to carbon material is from about 0.25 mmol/g to about 5 mmol/g;
agitating the mixture to form a modified carbon material.
17. A method as set forth in claim 16 further comprising:
separating the modified carbon material from the mixture; and fabricating the modified carbon material into a fuel cell component.

18. A method comprising:

forming a first mixture by mixing a carbon material suitable for use in a fuel cell component, an organic solvent, a reductant, and a compound having the general formula I—R in an amount such that the ratio of R to carbon material is from about 0.25 mmol/g to about 5 mmol/g, and wherein R comprises a perfluorosulfonic acid precursor molecule comprising a sulfonyl fluoride end group ($SO_2F$);

agitating the mixture to form a modified carbon material;

converting the sulfonyl fluoride end group to an end group comprising a sulfonate functional group;

converting the end group comprising a sulfonate functional group to a sulfonic acid end group.

19. A method as set forth in claim 18 wherein forming a mixture comprises mixing a compound with the formula I—R, wherein R comprises a perfluorosulfonic acid precursor molecule having the general formula $C_nF_{2n}SO_2F$ or $C_nF_{2n}OC_nF_{2n}SO_2F$ with $1 \leq n \leq 10$.

20. A method as set forth in claim 18 further comprising:

separating the modified carbon material from the mixture, and fabricating the modified carbon material into a fuel cell component.

* * * * *